(12) United States Patent
Wollenberg

(10) Patent No.: US 7,985,592 B2
(45) Date of Patent: Jul. 26, 2011

(54) HIGH THROUGHPUT SCREENING METHODS FOR LUBRICATING OIL COMPOSITIONS

(75) Inventor: Robert H. Wollenberg, Orinda, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 1884 days.

(21) Appl. No.: 10/779,421

(22) Filed: Feb. 13, 2004

(65) Prior Publication Data

US 2005/0181515 A1  Aug. 18, 2005

(51) Int. Cl.
*G01N 33/26* (2006.01)

(52) U.S. Cl. ............... 436/139; 506/12; 506/24; 506/33

(58) Field of Classification Search .................. None
See application file for complete search history.

(56) References Cited

U.S. PATENT DOCUMENTS

| | | | |
|---|---|---|---|
| 3,108,967 A * | 10/1963 | Bailey, Jr. ................ | 508/448 |
| 4,774,281 A * | 9/1988 | Chaffee et al. ............ | 524/588 |
| 5,062,980 A * | 11/1991 | Migdal et al. ............. | 508/291 |
| 5,308,522 A * | 5/1994 | Francisco et al. .......... | 508/281 |
| 5,814,110 A | 9/1998 | Bartz et al. | |
| 5,959,297 A | 9/1999 | Weinberg et al. | |
| 5,985,356 A | 11/1999 | Schultz et al. | |
| 6,004,617 A | 12/1999 | Schultz et al. | |
| 6,030,917 A | 2/2000 | Weinberg et al. | |
| 6,034,775 A | 3/2000 | McFarland et al. | |
| 6,045,671 A | 4/2000 | Wu et al. | |
| 6,087,181 A | 7/2000 | Cong | |
| 6,149,882 A | 11/2000 | Guan et al. | |
| 6,157,449 A | 12/2000 | Hajduk | |
| 6,175,409 B1 | 1/2001 | Nielsen et al. | |
| 6,182,499 B1 | 2/2001 | McFarland et al. | |
| 6,187,164 B1 | 2/2001 | Warren et al. | |
| 6,248,540 B1 | 6/2001 | Weinberg et al. | |
| 6,260,407 B1 | 7/2001 | Petro et al. | |
| 6,265,226 B1 | 7/2001 | Petro et al. | |
| 6,296,771 B1 | 10/2001 | Miroslav | |
| 6,326,090 B1 | 12/2001 | Schultz et al. | |
| 6,336,353 B2 | 1/2002 | Matsiev et al. | |
| 6,345,528 B2 | 2/2002 | Petro et al. | |
| 6,346,290 B1 | 2/2002 | Schultz et al. | |
| 6,371,640 B1 | 4/2002 | Hajduk et al. | |
| 6,373,570 B1 | 4/2002 | McFarland et al. | |
| 6,393,895 B1 | 5/2002 | Matsiev et al. | |
| 6,393,898 B1 | 5/2002 | Hajduk et al. | |

(Continued)

FOREIGN PATENT DOCUMENTS

EP  1318408  11/2003

(Continued)

OTHER PUBLICATIONS

International Search Report and Written Opinion in counterpart Singapore Patent Application No. 200605466-2.

(Continued)

*Primary Examiner* — Christopher M Gross

(57) ABSTRACT

Methods for determining the compatibility of a plurality of fluid samples of different lubricating oil compositions with elastomers is provided. Each sample includes one or more base oils of lubricating viscosity and one or more lubricating oil additives. The methods can advantageously be optimized using combinatorial chemistry, in which a database of combinations of lubricating oil compositions are generated. As market conditions vary and/or product requirements or customer specifications change, conditions suitable for forming desired products can be identified with little or no downtime.

21 Claims, 2 Drawing Sheets

U.S. PATENT DOCUMENTS

| | | |
|---|---|---|
| 6,395,552 B1 | 5/2002 | Borade et al. |
| 6,401,519 B1 | 6/2002 | McFarland et al. |
| 6,406,632 B1 | 6/2002 | Safir et al. |
| 6,410,331 B1 | 6/2002 | Schultz et al. |
| 6,419,881 B1 | 7/2002 | Weinberg et al. |
| 6,420,179 B1 | 7/2002 | Schultz et al. |
| 6,436,292 B1 | 8/2002 | Petro |
| 6,438,497 B1 | 8/2002 | Mansky et al. |
| 6,440,745 B1 | 8/2002 | Weinberg et al. |
| 6,441,901 B2 | 8/2002 | McFarland et al. |
| 6,461,515 B1 | 10/2002 | Safir et al. |
| 6,468,806 B1 | 10/2002 | McFarland et al. |
| 6,475,391 B2 | 11/2002 | Safir et al. |
| 6,484,567 B1 | 11/2002 | Hajduk et al. |
| 6,491,816 B2 | 12/2002 | Petro |
| 6,508,984 B1 | 1/2003 | Turner et al. |
| 6,519,032 B1 | 2/2003 | Kuebler et al. |
| 6,528,026 B2 | 3/2003 | Hajduk et al. |
| 6,535,284 B1 | 3/2003 | Hajduk et al. |
| 6,535,824 B1 | 3/2003 | Mansky et al. |
| 6,536,944 B1 | 3/2003 | Archibald et al. |
| 6,541,271 B1 | 4/2003 | McFarland et al. |
| 6,553,318 B2 | 4/2003 | Mansky |
| 6,576,906 B1 | 6/2003 | Archibald et al. |
| 6,577,392 B1 | 6/2003 | Nielsen et al. |
| 6,582,116 B2 | 6/2003 | Nielsen |
| 6,605,473 B1 | 8/2003 | Hajduk et al. |
| 6,644,101 B2 | 11/2003 | Hajduk et al. |
| 6,649,413 B1 | 11/2003 | Schultz et al. |
| 6,650,102 B2 | 11/2003 | Hajduk et al. |
| 6,653,138 B1 | 11/2003 | Turner et al. |
| 6,655,194 B2 | 12/2003 | Hajduk et al. |
| 6,658,429 B2 | 12/2003 | Dorsett, Jr. |
| 6,664,067 B1 | 12/2003 | Hajduk et al. |
| 6,668,622 B2 | 12/2003 | Hajduk et al. |
| 6,670,298 B1 | 12/2003 | Weinberg et al. |
| 6,679,130 B2 | 1/2004 | Hajduk et al. |
| 6,681,618 B2 | 1/2004 | Hajduk et al. |
| 6,686,205 B1 | 2/2004 | Schultz et al. |
| 6,690,179 B2 | 2/2004 | Hajduk et al. |
| 2002/0023507 A1 | 2/2002 | Hajduk et al. |
| 2002/0028456 A1 | 3/2002 | Mansky et al. |
| 2002/0029621 A1 | 3/2002 | Hajduk et al. |
| 2002/0032531 A1 | 3/2002 | Mansky et al. |
| 2002/0098332 A1 | 7/2002 | Warren et al. |
| 2002/0148282 A1 | 10/2002 | Hajduk et al. |
| 2002/0155036 A1 | 10/2002 | Hajduk et al. |
| 2002/0164275 A1 | 11/2002 | Wheeler et al. |
| 2003/0007152 A1 | 1/2003 | McFarland et al. |
| 2003/0032198 A1 | 2/2003 | Lugmair et al. |
| 2003/0032205 A1 | 2/2003 | McFarland et al. |
| 2003/0037601 A1 | 2/2003 | Mansky et al. |
| 2003/0037620 A1 | 2/2003 | Mansky |
| 2003/0041653 A1 | 3/2003 | Matsiev et al. |
| 2003/0041671 A1 | 3/2003 | Hajduk et al. |
| 2003/0041672 A1 | 3/2003 | Hajduk et al. |
| 2003/0041676 A1 | 3/2003 | Hajduk et al. |
| 2003/0054740 A1 | 3/2003 | Mansky |
| 2003/0055587 A1 | 3/2003 | Wang et al. |
| 2003/0056576 A1 | 3/2003 | Mansky |
| 2003/0068829 A1 | 4/2003 | Giaquinta et al. |
| 2003/0097871 A1 | 5/2003 | Mansky |
| 2003/0100119 A1 | 5/2003 | Weinberg et al. |
| 2003/0113797 A1 | 6/2003 | Jia et al. |
| 2003/0127776 A1 | 7/2003 | Carlson et al. |
| 2003/0133113 A1 | 7/2003 | Hajduk et al. |
| 2003/0138025 A1 | 7/2003 | Archibald et al. |
| 2003/0141613 A1 | 7/2003 | Hajduk et al. |
| 2003/0142309 A1 | 7/2003 | Kuebler et al. |
| 2003/0157721 A1 | 8/2003 | Turner et al. |
| 2003/0161763 A1 | 8/2003 | Erden et al. |
| 2003/0169638 A1 | 9/2003 | Nielsen |
| 2003/0190260 A1 | 10/2003 | Wheeler et al. |
| 2003/0203500 A1 | 10/2003 | Carlson et al. |
| 2003/0211016 A1 | 11/2003 | Dales et al. |
| 2003/0218467 A1 | 11/2003 | Carlson et al. |
| 2003/0219906 A1 | 11/2003 | Giaquinta et al. |
| 2004/0074452 A1* | 4/2004 | Guinther et al. ............. 123/1 A |
| 2004/0123650 A1 | 7/2004 | Kolosov et al. |
| 2008/0153716 A1* | 6/2008 | Wollenberg et al. ........... 506/40 |

FOREIGN PATENT DOCUMENTS

WO     WO 02/07870     1/2002

OTHER PUBLICATIONS

International Search Report and Written Opinion in counterpart Singapore Patent Application No. 200605466-2, 2008.

* cited by examiner

HIGH THROUGHPUT SCREENING METHODS FOR LUBRICATING OIL COMPOSITIONS

BACKGROUND OF THE INVENTION

1. Technical Field

The present invention relates generally to methods for high throughput screening of lubricating oil compositions.

2. Description of the Related Art

The use of a combinatorial approach for materials synthesis is a relatively new area of research aimed at using rapid synthesis and screening methods to build libraries of polymeric, inorganic or solid state materials. For example, advances in reactor technology have empowered chemists and engineers to rapidly produce large libraries of discrete organic molecules in the pursuit of new drug discovery, which have led to the development of a growing branch of research called combinatorial chemistry. Combinatorial chemistry generally refers to methods and materials for creating collections of diverse materials or compounds—commonly known as libraries—and to techniques and instruments for evaluating or screening libraries for desirable properties.

Presently, research in the lubricant industry involves individually forming candidate lubricating oil compositions and then performing a macro-scale analysis of the candidate compositions by employing a large amount of the candidate to be tested. Additionally, the methods employed for testing each candidate composition require manual operation. This, in turn, significantly reduces the number of compositions that can be tested and identified as leading compositions.

Drawbacks associated with conventional screening procedures can be seen as follows. For example, governmental and automotive industry pressure towards reducing the phosphorous and sulfur content of lubricating oil compositions used as, for example, passenger car and heavy duty diesel engine oils, is leading to new research to identify oil compositions which can satisfy certain tests such as, for example, oxidation, wear and compatibility tests, while containing low levels of phosphorous and sulfur. In this context, United States Military Standards MIL-L-46152E and the ILSAC Standards defined by the Japanese and United States Automobile Industry Association at present require the phosphorous content of engine oils to be at or below 0.10 wt. % with future phosphorous content being proposed to even lower levels, e.g., 0.08 wt. % by June, 2004 and below 0.05 wt. % by January, 2006. Also, at present, there is no industry standard requirement for sulfur content in engine oils, but it has been proposed that the sulfur content be below 0.3 wt. % to meet June, 2007 requirements for emissions. Thus, it would be desirable to decrease the amount of phosphorous and sulfur in lubricating oils still further, thereby meeting future industry standard proposed phosphorous and sulfur contents in the engine oil while still retaining the oxidation or corrosion inhibiting properties and antiwear properties of the higher phosphorous and sulfur content engine oils. In order to accomplish this, a large number of proposed lubricating oil compositions must be tested to determine which compositions may be useful.

Additionally, similar changes in specifications and changing customer needs also drive reformulation efforts in other lubricant applications such as, for example, transmission fluids, hydraulic fluids, gear oils, marine cylinder oils, compressor oils, refrigeration lubricants and the like.

However, as stated above, present research in the lubricant industry does not allow for reformulation to occur in an expeditious manner. As such, there exists a need in the art for a more efficient, economical and systematic approach for the preparation of lubricating oil compositions and screening of such compositions. For example, a problem facing lubricant manufacturers is that of seal deterioration in the engine. All internal combustion engines use elastomer seals such as, for example, viton seals, in their assembly. During use, these elastomer seals are susceptible to serious deterioration from lubricating oil additive compositions and lubricating oil compositions under engine operating conditions. Deterioration in the seals results in brittleness and cracking of the seals causing oil to leak from the engine. A lubricating oil composition that degrades the elastomer seals in an engine is unacceptable to engine manufacturers.

Another example of elastomer compatibility is in elastomeric electrical cable accessories which are installed, for example, over cables, metallic contacts or mated in complimentary designs such as elbows and bushings, connectors, splices, switches, fuses, junctions and a wide variety of other configurations. Cable accessories are usually based on ethylene-propylene elastomers, e.g., ethylene-propylene rubber (EPR) and ethylene propylene diene monomer (also referred to as ethylene propylene diene methyl or EPDM), and are typically lubricated with silicone-based oils and greases. In almost every design, installation requires interfaces to slide against each other with corresponding frictional forces. Because these components are elastomeric, these frictional forces are very high. Thus lubrication of these interfaces is a necessity. The most common lubricants are oils and greases, typically based on a compatibility with the type of elastomer requiring lubrication. Silicone oils and greases exhibit excellent electrical characteristics and are very compatible with ethylene-propylene based elastomers. These lubricants are usually supplied by the manufactures at significant cost as a separate package with the cable accessories.

Generally, cable accessories have approximately a thirty to forty year life span, and many have separable interfaces used for connection and disconnection. Although many oils and greases are high quality and are used effectively for many years of service, they often lose their lubricating capacity over time. Due to the inherent mobility of the oils used in these lubricants, they tend to "bleed" and/or migrate away from the interface. Consequently, the interface "dries out" and exposes the high coefficient of friction elastomeric surface. The result is component sticking which is a major problem in the industry.

Accordingly, it would be desirable to rapidly screen a plurality of sample candidate lubricating oil compositions for compatibility with elastomers utilizing small amounts of each sample. In this manner, a high throughput preparation and screening of a vast number of diverse compositions can be achieved to identify which compositions are substantially compatible with elastomers.

SUMMARY OF THE INVENTION

A high throughput screening method for determining the compatibility of lubricating oil compositions with elastomers is provided herein. In accordance with one embodiment of the present invention, a high throughput method for screening lubricating oil compositions for compatibility with an elastomer, under program control, is provided comprising the steps of (a) providing a plurality of different lubricating oil composition samples, each sample comprising (i) a major amount of at least one base oil of lubricating viscosity and (ii) a minor amount of at least one lubricating oil additive; (b) providing at least one elastomer; (c) measuring the compatibility of each sample with the elastomer to provide elastomer compatibility data for each sample; and, (c) outputting the results of step (b).

In a second embodiment of the present invention, a system for determining the compatibility of lubricating oil composition samples with elastomers, under program control, is provided comprising:

a) a plurality of test receptacles, each receptacle containing a different lubricating oil composition sample comprising (i) a major amount of at least one base oil of lubricating viscosity and (ii) a minor amount of at least one lubricating oil additive;

b) receptacle moving means for individually positioning the test receptacles in a testing station for measurement of elastomer compatibility of the respective sample with at least one elastomer;

c) elastomer moving means for individually positioning at least one elastomer in the testing station for measurement of elastomer compatibility with the respective sample;

d) means for measuring the elastomer compatibility of the sample with the elastomer in the testing station to obtain elastomer compatibility data associated with the sample and for transferring the elastomer compatibility data to a computer controller.

The methods and systems of the present invention advantageously permit the screening of many different composition samples in an efficient manner to determine compatibility of the samples with elastomers, e.g., fluorocarbon elastomer seals.

BRIEF DESCRIPTION OF THE DRAWINGS

Various embodiments are described below with reference to the drawings wherein.

DETAILED DESCRIPTION OF THE PREFERRED EMBODIMENT(S)

Figure 1:
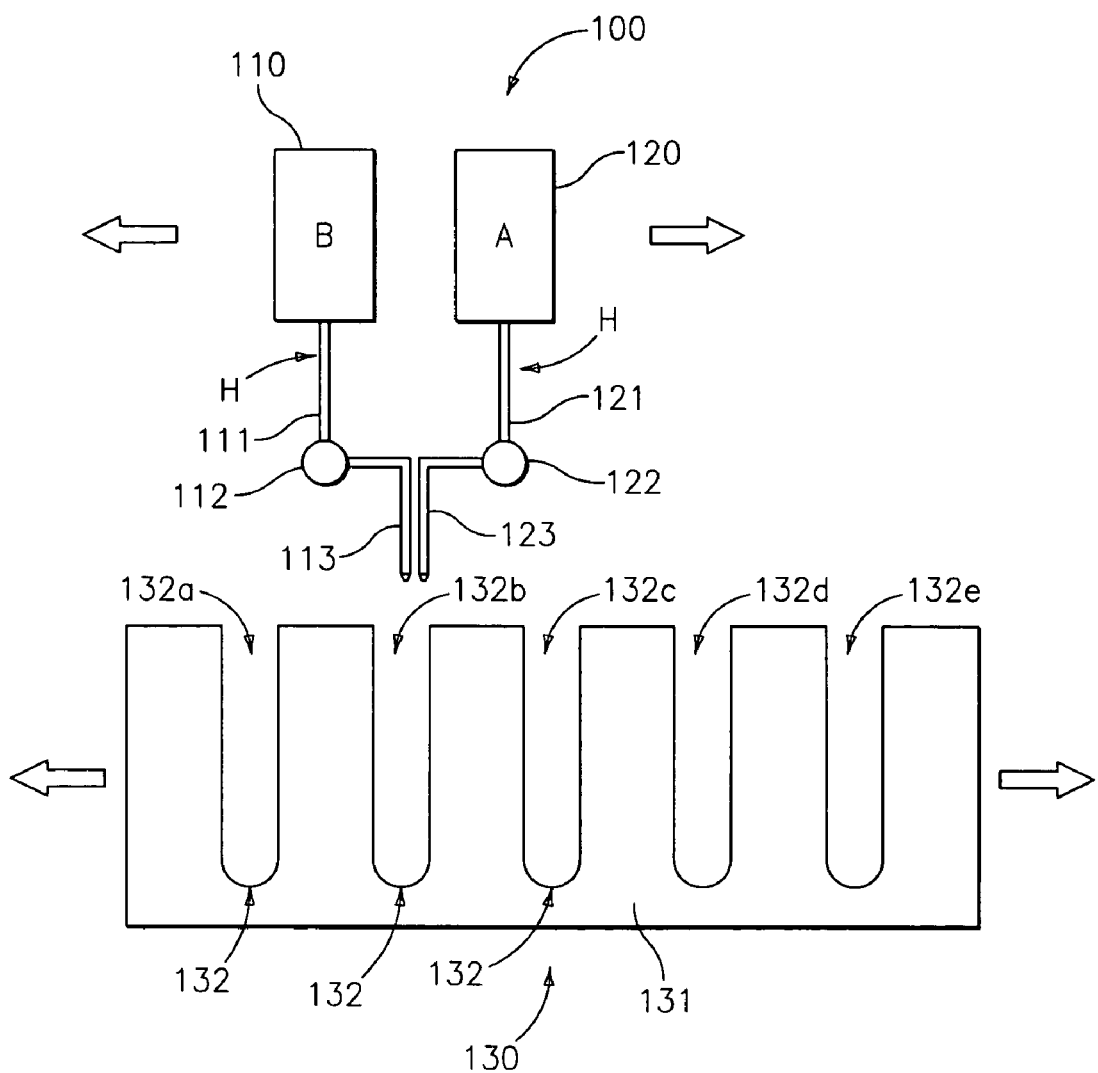
FIG. 1 is a schematic diagram of a system for preparing a plurality of different lubricating oil compositions; and, FIG. 2 is a schematic diagram of a system for measuring elastomer compatibility of a plurality of samples of lubricating oil compositions.

The present invention is directed to a high throughput screening method for determining the compatibility of lubricating oil compositions with elastomers. The expression "high throughput" as used herein shall be understood to mean that a relatively large number of different lubricating oil compositions can be rapidly prepared and analyzed. In a first step of one embodiment of the screening method of the present invention, at least one lubricating oil composition is introduced in a plurality of respective test receptacles so that each receptacle contains a different lubricating oil composition having a different composition depending upon the percentage amounts and/or types of the at least one base oil and/or at least one additive combined in each receptacle.

Data regarding the composition of each sample are stored in a data library. Adding the information related to the elastomer compatibility data of each of the stored compositions substantially facilitates the selection of candidate compositions capable of successfully carrying out the elastomer compatibility tests under the desired operating conditions or statutory requirements. Accordingly, storing this information in the combinatorial library not only allows for a rapid selection of multiple lubricating oil compositions in response to new requirements for a given test, but also becomes another piece of information in addition to, for example, storage stability, oxidation stability, wear stability, dispersancy data, deposit formation data, etc., of the cataloged compositions. This information may also allow for calculating necessary changes of the additives at the least cost. The procedure is advantageously accomplished under program control and automatically controlled by, for example, a microprocessor or other computer control device. The expression "program control" as used herein shall be understood to mean the equipment used herein in providing the plurality of lubricating oil compositions is automated and controlled by a microprocessor or other computer control device.

The lubricating oil compositions for use in the high throughput screening method of this invention include at least one base oil of lubricating viscosity and at least one lubricating oil additive. Generally, the lubricating oil compositions for use in the high throughput screening method of this invention include a minor amount of at least one lubricating oil additive together with a major amount of at least one base oil of lubricating viscosity, e.g., an amount of greater than 50 wt. %, preferably greater than about 70 wt. %, more preferably from about 80 to about 99.5 wt. % and most preferably from about 85 to about 98 wt. %, based on the total weight of the composition.

The expression "base oil" as used herein shall be understood to mean a base stock or blend of base stocks which is a lubricant component that is produced by a single manufacturer to the same specifications (independent of feed source or manufacturer's location): that meets the same manufacturer's specification; and that is identified by a unique formula, product identification number, or both. The base oil for use herein can be any presently known or later-discovered base oil of lubricating viscosity used in formulating lubricating oil compositions for any and all such applications, e.g., engine oils, marine cylinder oils, natural gas engine oils, railroad oils, two-cycle engine oils, tractor oils, heavy duty diesel engine oils, truck oils and functional fluids such as hydraulic oils, gear oils, transmission fluids, etc. Additionally, the base oils for use herein can optionally contain viscosity index improvers, e.g., polymeric alkylmethacrylates; olefinic copolymers, e.g., an ethylene-propylene copolymer or a styrene-butadiene copolymer; and the like and mixtures thereof.

As one skilled in the art would readily appreciate, the viscosity of the base oil is dependent upon the application. Accordingly, the viscosity of a base oil for use herein will ordinarily range from about 2 to about 2000 centistokes (cSt) at 100° Centigrade (C.). Generally, individually the base oils used as engine oils will have a kinematic viscosity range at 100° C. of about 2 cSt to about 30 cSt, preferably about 3 cSt to about 16 cSt, and most preferably about 4 cSt to about 12 cSt and will be selected or blended depending on the desired end use and the additives in the finished oil to give the desired grade of engine oil, e.g., a lubricating oil composition having an SAE Viscosity Grade of 0W, 0W-20, 0W-30, 0W-40, 0W-50, 0W-60, 5W, 5W-20, 5W-30, 5W-40, 5W-50, 5W-60, 10W, 10W-20, 10W-30, 10W-40, 10W-50, 15W, 15W-20, 15W-30 or 15W-40. Oils used as gear oils can have viscosities ranging from about 2 cSt to about 2000 cSt at 100° C.

Base stocks may be manufactured using a variety of different processes including, but not limited to, distillation, solvent refining, hydrogen processing, oligomerization, esterification, and rerefining. Rerefined stock shall be substantially free from materials introduced through manufacturing, contamination, or previous use. The base oil of the lubricating oil compositions of this invention may be any natural or synthetic lubricating base oil. Suitable hydrocarbon synthetic oils include, but are not limited to, oils prepared from the polymerization of ethylene or from the polymerization of 1-olefins to provide polymers such as polyalphaolefin or PAO oils, or from hydrocarbon synthesis procedures using carbon monoxide and hydrogen gases such as in a Fisher-Tropsch process. For example, a suitable base oil is one that comprises little, if any, heavy fraction; e.g., little, if any, lube oil fraction of viscosity 20 cSt or higher at 100° C.

The base oil may be derived from natural lubricating oils, synthetic lubricating oils or mixtures thereof. Suitable base oil includes base stocks obtained by isomerization of synthetic wax and slack wax, as well as hydrocracked base stocks produced by hydrocracking (rather than solvent extracting) the aromatic and polar components of the crude. Suitable base oils include those in all API categories I, II, III, IV and V as defined in API Publication 1509, 14th Edition, Addendum I, December 1998. Group IV base oils are polyalphaolefins (PAO). Group V base oils include all other base oils not included in Group I, II, III, or IV. Although Group II, III and IV base oils are preferred for use in this invention, these preferred base oils may be prepared by combining one or more of Group I, II, III, IV and V base stocks or base oils.

Useful natural oils include mineral lubricating oils such as, for example, liquid petroleum oils, solvent-treated or acid-treated mineral lubricating oils of the paraffinic, naphthenic or mixed paraffinic-naphthenic types, oils derived from coal or shale, animal oils, vegetable oils (e.g., rapeseed oils, castor oils and lard oil), and the like.

Useful synthetic lubricating oils include, but are not limited to, hydrocarbon oils and halo-substituted hydrocarbon oils such as polymerized and interpolymerized olefins, e.g., polybutylenes, polypropylenes, propylene-isobutylene copolymers, chlorinated polybutylenes, poly(1-hexenes), poly(1-octenes), poly(1-decenes), and the like and mixtures thereof; alkylbenzenes such as dodecylbenzenes, tetradecylbenzenes, dinonylbenzenes, di(2-ethylhexyl)-benzenes, and the like; polyphenyls such as biphenyls, terphenyls, alkylated polyphenyls, and the like; alkylated diphenyl ethers and alkylated diphenyl sulfides and the derivative, analogs and homologs thereof and the like.

Other useful synthetic lubricating oils include, but are not limited to, oils made by polymerizing olefins of less than 5 carbon atoms such as ethylene, propylene, butylenes, isobutene, pentene, and mixtures thereof. Methods of preparing such polymer oils are well known to those skilled in the art.

Additional useful synthetic hydrocarbon oils include liquid polymers of alpha olefins having the proper viscosity. Especially useful synthetic hydrocarbon oils are the hydrogenated liquid oligomers of $C_6$ to $C_{12}$ alpha olefins such as, for example, 1-decene trimer.

Another class of useful synthetic lubricating oils include, but are not limited to, alkylene oxide polymers, i.e., homopolymers, interpolymers, and derivatives thereof where the terminal hydroxyl groups have been modified by, for example, esterification or etherification. These oils are exemplified by the oils prepared through polymerization of ethylene oxide or propylene oxide, the alkyl and phenyl ethers of these polyoxyalkylene polymers (e.g., methyl poly propylene glycol ether having an average molecular weight of 1,000, diphenyl ether of polyethylene glycol having a molecular weight of 500-1000, diethyl ether of polypropylene glycol having a molecular weight of 1,000-1,500, etc.) or mono- and polycarboxylic esters thereof such as, for example, the acetic esters, mixed $C_3$-$C_8$ fatty acid esters, or the $C_{13}$oxo acid diester of tetraethylene glycol.

Yet another class of useful synthetic lubricating oils include, but are not limited to, the esters of dicarboxylic acids e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acids, alkyl malonic acids, alkenyl malonic acids, etc., with a variety of alcohols, e.g., butyl alcohol, hexyl alcohol, dodecyl alcohol, 2-ethylhexyl alcohol, ethylene glycol, diethylene glycol monoether, propylene glycol, etc. Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include, but are not limited to, those made from carboxylic acids having from about 5 to about 12 carbon atoms with alcohols, e.g., methanol, ethanol, etc., polyols and polyol ethers such as neopentyl glycol, trimethylol propane, pentaerythritol, dipentaerythritol, tripentaerythritol, and the like.

Silicon-based oils such as, for example, polyalkyl-, polyaryl-, polyalkoxy- or polyaryloxy-siloxane oils and silicate oils, comprise another useful class of synthetic lubricating oils. Specific examples of these include, but are not limited to, tetraethyl silicate, tetra-isopropyl silicate, tetra-(2-ethylhexyl)silicate, tetra-(4-methyl-hexyl)silicate, tetra-(p-tert-butylphenyl)silicate, hexyl-(4-methyl-2-pentoxy)disiloxane, poly(methyl)siloxanes, poly(methylphenyl)siloxanes, and the like. Still yet other useful synthetic lubricating oils include, but are not limited to, liquid esters of phosphorous containing acids, e.g., tricresyl phosphate, trioctyl phosphate, diethyl ester of decane phosphionic acid, etc., polymeric tetrahydrofurans and the like.

The lubricating oil may be derived from unrefined, refined and rerefined oils, either natural, synthetic or mixtures of two or more of any of these of the type disclosed hereinabove. Unrefined oils are those obtained directly from a natural or synthetic source (e.g., coal, shale, or tar sands bitumen) without further purification or treatment. Examples of unrefined oils include, but are not limited to, a shale oil obtained directly from retorting operations, a petroleum oil obtained directly from distillation or an ester oil obtained directly from an esterification process, each of which is then used without further treatment. Refined oils are similar to the unrefined oils except they have been further treated in one or more purification steps to improve one or more properties. These purification techniques are known to those of skill in the art and include, for example, solvent extractions, secondary distillation, acid or base extraction, filtration, percolation, hydrotreating, dewaxing, etc. Rerefined oils are obtained by treating used oils in processes similar to those used to obtain refined oils. Such rerefined oils are also known as reclaimed or reprocessed oils and often are additionally processed by techniques directed to removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst.

Natural waxes are typically the slack waxes recovered by the solvent dewaxing of mineral oils; synthetic waxes are typically the wax produced by the Fischer-Tropsch process.

The second component of the compositions herein is at least one lubricating oil additive which can be any presently known or later-discovered additive used in formulating lubricating oil compositions. The lubricating oil additives for use herein include, but are not limited to, antioxidants, anti-wear agents, detergents such as metal detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and the like and mixtures thereof. Greases will require the addition of appropriate thickeners. A variety of the additives are known and commercially available. These additives, or their analogous compounds, can be employed for the preparation of the various lubricating oil compositions herein.

Alternatively, the lubricating oil additive(s) can further contain a diluent oil to form an additive concentrate. These concentrates usually include at least from about 98 wt. % to about 10 wt. %, preferably from about 98 wt. % to about 25 wt. % and most preferably from about 97 wt. % to about 50 wt. % of a diluent oil and from about 2 wt. % to about 90 wt. %, preferably from about 2 wt. % to about 75 wt. % and most preferably from about 3 wt. % to about 50 wt. %, of the foregoing additive(s). Suitable diluents for the concentrates include any inert diluent, preferably an oil of lubricating viscosity such as, for example, a base oil as described hereinbelow, so that the concentrate may be readily mixed with lubricating oils to prepare lubricating oil compositions. Suitable lubricating oils that may be used as diluents can be any oil of lubricating viscosity.

Examples of antioxidants include, but are not limited to, aminic types, e.g., diphenylamine, phenyl-alpha-napthylamine, N,N-di(alkylphenyl)amines; and alkylated phenylene-diamines; phenolics such as, for example, BHT, sterically hindered alkyl phenols such as 2,6-di-tert-butylphenol, 2,6-di-tert-butyl-p-cresol and 2,6-di-tert-butyl-4-(2-octyl-3-propanoic)phenol; sulfur-containing materials, e.g., sulfurized olefins or esters and the like and mixtures thereof.

Examples of antiwear agents include, but are not limited to, zinc dialkyldithiophosphates and zinc diaryldithiophosphates, e.g., those described in an article by Born et al. entitled "Relationship between Chemical Structure and Effectiveness of Some Metallic Dialkyl- and Diaryl-dithiophosphates in Different Lubricated Mechanisms", appearing in Lubrication Science 4-2 January 1992, see for example pages 97-100; aryl phosphates and phosphites, sulfur-containing esters, phosphosulfur compounds, metal or ash-free dithiocarbamates, xanthates, alkyl sulfides and the like and mixtures thereof.

Examples of detergents include, but are not limited to, overbased or neutral detergents such as sulfonate detergents, e.g., those made from alkyl benzene and fuming sulfuric acid; phenates (high overbased or low overbased), high overbased phenate stearates, phenolates, salicylates, phosphonates, thiophosphonates, ionic surfactants and the like and mixtures thereof. Low overbased metal sulfonates typically have a total base number (TBN) of from about 0 to about 30 and preferably from about 10 to about 25. Low overbased metal sulfonates and neutral metal sulfonates are well known in the art.

Examples of rust inhibitors include, but are not limited to, nonionic polyoxyalkylene agents, e.g., polyoxyethylene lauryl ether, polyoxyethylene higher alcohol ether, polyoxyethylene nonylphenyl ether, polyoxyethylene octylphenyl ether, polyoxyethylene octyl stearyl ether, polyoxyethylene oleyl ether, polyoxyethylene sorbitol monostearate, polyoxyethylene sorbitol monooleate, and polyethylene glycol monooleate; stearic acid and other fatty acids; dicarboxylic acids; metal soaps; fatty acid amine salts; metal salts of heavy sulfonic acid; partial carboxylic acid ester of polyhydric alcohol; phosphoric esters; (short-chain)alkenyl succinic acids; partial esters thereof and nitrogen-containing derivatives thereof; synthetic alkarylsulfonates, e.g., metal dinonylnaphthalene sulfonates; and the like and mixtures thereof.

Examples of friction modifiers include, but are not limited to, alkoxylated fatty amines; borated fatty epoxides; fatty phosphites, fatty epoxides, fatty amines, borated alkoxylated fatty amines, metal salts of fatty acids, fatty acid amides, glycerol esters, borated glycerol esters; and fatty imidazolines as disclosed in U.S. Pat. No. 6,372,696, the contents of which are incorporated by reference herein; friction modifiers obtained from a reaction product of a $C_4$ to $C_{75}$, preferably a $C_6$ to $C_{24}$, and most preferably a $C_6$ to $C_{20}$, fatty acid ester and a nitrogen-containing compound selected from the group consisting of ammonia, and an alkanolamine, e.g., those disclosed in U.S. Ser. No. 10/402,170, filed Mar. 28, 2003, the contents of which are incorporated by reference herein, and the like and mixtures thereof.

Examples of antifoaming agents include, but are not limited to, polymers of alkyl methacrylate; polymers of dimethylsilicone and the like and mixtures thereof.

Examples of ashless dispersants include, but are not limited to, polyalkylene succinic anhydrides; non-nitrogen containing derivatives of a polyalkylene succinic anhydride; a basic nitrogen compound selected from the group consisting of succinimides, carboxylic acid amides, hydrocarbyl monoamines, hydrocarbyl polyamines, Mannich bases, phosphonamides, thiophosphonamides and phosphoramides; thiazoles, e.g., 2,5-dimercapto-1,3,4-thiadiazoles, mercaptobenzothiazoles and derivatives thereof; triazoles, e.g., alkyltriazoles and benzotriazoles; copolymers which contain a carboxylate ester with one or more additional polar function, including amine, amide, imine, imide, hydroxyl, carboxyl, and the like, e.g., products prepared by copolymerization of long chain alkyl acrylates or methacrylates with monomers of the above function; and the like and mixtures thereof. The derivatives of these dispersants, e.g., borated dispersants such as borated succinimides, and ethylene carbonate post treated succinimides may also be used. Preferably, the dispersants are polyalkylene succinimides derived from animation of polyalkylene succinic anhydrides with polyalkylene polyamine.

If desired, prior to dispensing the at least one base oil and at least one lubricating oil additive to provide the compositions herein, as discussed hereinbelow, it can be advantageous to conduct molecular modeling of proposed compounds for use in the compositions (i.e., formulations) to determine which compounds may provide potential leading candidate compositions. For example, calculations can be carried out involving such factors as, for example, transition states, bond lengths, bond angles, dipole moment, hydrophobicity, etc, of the compounds. This can be carried out using known software such as, for example, Quantum Mechanics available from Accelrys (San Diego, Calif.).

Software for the design of test libraries can be used to design the original compound test libraries based on input from the foregoing experimental program(s). This software can be used to efficiently design test libraries that cover the desired experimental space and utilize statistical experimental design methods. Other software can then be used to analyze the data from the experiments and correlate that data with the structure of the compounds and/or compound treatment conditions and/or reaction conditions. Such correlations are often referred to as QSAR software (Quantitative Structure Activity Relations) available from Accelrys (San Diego, Calif.). Such QSAR programs can then be used by the software to design subsequent compound test libraries for further screening.

The use of such QSAR programs can add to the efficiency of screening. As more data is collected, these QSAR programs can become more efficient at developing compound libraries with increased probability for finding desirable compounds. For example, the compounds analyzed can be formulated into various lubricating oil compositions, as described hereinbelow, and then further analyzed by way of, for example, regression and analysis technologies, using known software, e.g., $C^2$-QSAR available from Accelrys (San Diego, Calif.). In this manner, validation of the data obtained from the molecular modeling can be achieved and then this data can also be stored in a data collector. In this way, new compounds, conceived by one skilled in the art can be checked by the QSAR software to predict their activity prior to their actual synthesis. Additionally, such software tools may be utilized to prioritize a list of possible compounds being considered for synthesis in such a way that one skilled in the art will have a higher probability for success.

Referring now to FIG. 1, an example of a system to provide the foregoing compositions in the plurality of respective test receptacles is generally illustrated as system 100. Representative of this system and method for providing the foregoing compositions in the plurality of respective test receptacles is one disclosed in co-pending U.S. patent application Ser. No. 10/699,510, filed on Oct. 31, 2003 and entitled "HIGH THROUGHPUT PREPARATION OF LUBRICATING OIL COMPOSITIONS FOR COMBINATORIAL LIBRARIES" by Wollenberg et al. and having a common assignee with the present application, the contents of which are incorporated by reference herein. It is to be understood that the present invention is not limited to this system and that other systems can be envisioned for providing the foregoing compositions in the plurality of respective test receptacles.

Generally, vessel 110 contains a supply of the foregoing base oils of lubricating viscosity B. Vessel 120 contains a supply of additive A, which can be any of the foregoing additives useful for modifying the properties of the base oil. As one skilled in the art would readily appreciate, one or more of vessels 110 and vessels 120 can be used when dispensing more than one base oil and/or more than one additive, respectively.

Tubular line 111 is a conduit for communicating the base oil B to nozzle portion 113, from which it can be dispensed into a selected test reservoir, as described below. The amount of base oil dispensed is determined by metering pump 112, which can be computer controlled.

Tubular line 121 is a conduit for communicating the lubricating oil additive A to nozzle portion 123, from which it can be dispensed into a selected test reservoir, as described below. The amount of lubricating oil additive dispensed is determined by metering pump 122, which also can be computer controlled. Computer programs and systems for automatically metering predetermined amounts of materials in accordance with a preselected protocol are known in the art and can be used herein.

Nozzles 113 and 123 are preferably in close proximity so that base oil B and additive A can be simultaneously dispensed in a test reservoir. Alternatively, base oil B and additive A can be sequentially added to the test reservoir. The nozzles 113 and 123 can comprise a multichannel pipette or one or more syringe needles.

The vessels 110 and 120 can be under pressure. Optionally, more than two vessels can be employed. Metering pumps suitable for use in the invention are known and commercially available. In the event that highly viscous lubricant base stock or additives are used, the vessels 110 and 120 and/or the tubular lines 111 and 121, metering pumps 112 and 122, and/or nozzles 113 and 123 can be heated to facilitate fluid flow therethrough.

The test frame 130 includes a block 131 of transparent material (e.g., glass) having a plurality of recesses 132 for receiving the dispensed base oil and additives. The recesses provide test reservoirs wherein each reservoir contains lubricating oil compositions of a different and predetermined composition, i.e., the percentage and/or type of base oil and/or additives in each composition will vary from one reservoir to another. Optionally, the reservoirs can be individual receptacles (e.g., test tubes) mounted upon a rack, instead of being recesses in a block. Preferably, the test receptacles comprise transparent glass tubes. While five reservoirs, i.e., recesses 132a, 132b, 132c, 132d, 132e, are illustrated in FIG. 1, any number of reservoirs can be employed herein. For example the system can employ 20, 50, 100 or even more test receptacles and samples as required.

The individual reservoirs are adapted to hold relatively small amounts of lubricating oil samples. The sample size in each reservoir can generally be less than about 50 ml, preferably no more than about 20 ml, preferably no more than about 15 ml, more preferably no more than about 10 ml and yet more preferably no more than about 5 ml.

The test frame 130 and dispensing nozzles 113 and 123 are movable relative to one another. Although manual movement of the apparatus by an equipment operator is within the purview of the invention, robotic mechanisms with programmable movement are preferred. In one embodiment the test frame 130 is mounted upon a slidable carriage movable in a lateral and/or vertical direction so as to sequentially position a selected recess under the dispensing nozzles 113 and 123. In another embodiment, the nozzles 113 and 123, and optionally the vessels 110 and 120, are slidably movable laterally and/or vertically to accomplish positioning of the nozzles 113 and 123.

In a testing procedure, vessels 110 and 120 are filled with the selected lubricant base oil and additive(s), respectively. The apparatus of system 100 is moved such that dispensing nozzles 113 and 123 are positioned above and in alignment with recess 132a. A metered amount of base oil B and a metered amount of additive A are simultaneously dispensed into recess 132a. The dispensing nozzles 113 and 123 are thereafter repositioned to be in alignment with the next recess 132b and the metered amounts of additive A and/or base oil B are changed in accordance with a predetermined schedule of variation such that the lubricating oil in recess 132b has a different percentage composition of additive than that in recess 132a. The pattern is repeated as the nozzles 113 and 123 are sequentially aligned with the successive recesses 132c, 132d, and 132e so that each recess has a predetermined composition of lubricating oil.

The components A and B are preferably combined in the reservoirs by mixing, for example, by agitation of the frame 131, static mixing, individual stirring of the contents of the reservoirs (mechanical or magnetic stirring) and/or by bubbling the reservoir with gas, e.g., nitrogen. Optionally, base oil B and additive(s) A can be combined prior to dispensing into the respective reservoirs. For example, a single dispensing nozzle having a mixing chamber can be used, wherein base oil B and additive(s) A are metered into the mixing chamber and then dispensed through the nozzle into the reservoir.

Once the plurality of receptacles have been provided containing the lubricating oil compositions, the plurality of fluid samples can then be analyzed for compatibility with an elastomer, e.g., elastomer tensile strength measurement, elastomer elongation measurement, etc. Elastomers for use herein can be any can be any presently known or later-discovered elastomer for any and all such applications.

Examples of such elastomers include, but are not limited to, olefinic elastomers, e.g., polyolefin elastomers produced from, for example, copolymers of ethylene and propylene (EP), terpolymers of, for example, ethylene, propylene and a diene (EPDM), etc.; styrenic elastomers; polyacrylate elastomers; poly(ether/ester) elastomers; natural or synthetic rubbers, e.g., nitrile rubbers, silicone rubbers, neoprene rubbers, etc.; elastomer seals, e.g., Viton® polymers (fluorocarbon elastomers), Vamac® polymers etc.; and the like and mixtures thereof.

Figure 2:
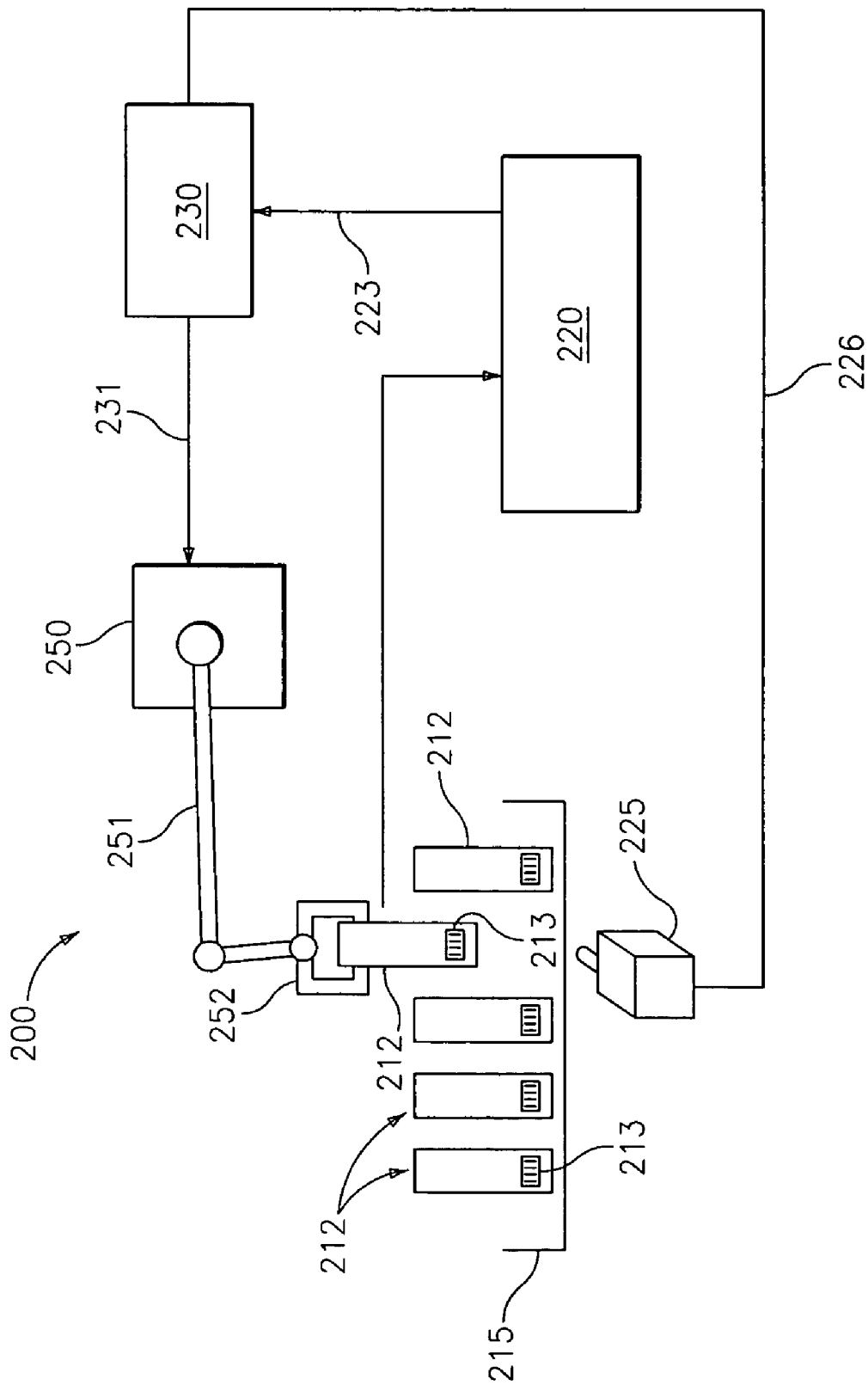

Referring now to FIG. 2, a system for sequentially analyzing a plurality of fluid samples for elastomer compatibility is schematically illustrated. The samples can include lubricating oil compositions containing one or more base oils and one or more lubricating oil additives, such as those described herein. System 200 is schematically illustrated wherein an array of test receptacles 212 are mounted in a holder 215. The system 200 is adapted to accommodate any number of test receptacles 212 (and samples). Each sample is identifiable, for example, by the position of its test receptacle in an ordered array in holder 215, or more preferably by having an identifying mark associated with it. For example, each test receptacle 212 can include an identifying bar code 213 affixed to the outer surface thereof. A bar code reader 225 is positioned so as to be able to read the individual bar codes of the respective test receptacles 212 and to transmit a bar code data signal to a computer controller 230 via a data transmission line 226 to electronically identify the sample. The bar code reader 225 is preferably movable with respect to the holder 215 in response to a signal from computer controller 230 so as to be positionable in alignment with selected individual test receptacles 212.

A robotic assembly 250 includes a movable arm 251 with a grasping mechanism 252. The robotic assembly is adapted to grasp an individual test receptacle 212 in accordance with selection instructions from computer controller 230 and move the test receptacle to a position in testing station 220 so that the sample in the receptacle can be measured for elastomer comparability data. The robotic assembly is also adapted to grasp the elastomer (not shown) to be tested with the lubricating sample in accordance with selection instructions from computer controller 230 and move the elastomer to a position in testing station 220 so that testing of the elastomer and sample can be carried out. The computer controller 230 is operatively associated with controls to the robotic assembly via control signal transmission line 231 to selectively retrieve predetermined test receptacles and elastomers for measurement and then replace them in their assigned respective positions in the holder.

Testing station 220 includes means for testing the samples for the compatibility with an elastomer. Elastomer compatibility data results of the test are converted to an electrical or optical signal and transmitted via signal transmission line 223 to computer controller 230. Various means for elastomer compatibility testing are known and generally include subjecting the sample to elastomer degradation conditions and measuring the elastomer compatibility, e.g., elastomer tensile strength measurement, elastomer elongation measurement, etc, of the sample over a predetermined period of time.

For example, in an embodiment of a test method for use herein (e.g., Volkswagon PV 3344 Viton Seal Compatibility Test) the elastomer specimens are immersed into a sufficient amount of the test lubricating oil composition samples, e.g., a volume of sample:volume of elastomer of about 50:1 to about 90:1, at a predetermined temperature for a predetermined time. If desired, prior to carrying out this test the elastomer specimens can be thermally conditioned at a temperature of about 100° C. to about 200° C. for a period of time ranging from about 20 hours to about 60 hours to drive off any moisture which is readily absorbed by the filler component of the elastomer as known in the art.

The predetermined temperature can vary widely depending the specific environment being simulated for the elastomer and sample and will ordinarily range from about 100° C. to about 400° C. and preferably from about 125° C. to about 200° C. The test is ordinarily conducted for a time period of about 100 hours to about 400 hours and preferably from about 200 to about 300 hours. If desired, the test can be broken up into intervals wherein the lubricating sample is replaced with a fresh sample after a specific time period. At the completion of the testing period, the elastomer specimens are then evaluated for elastomer compatability data, e.g., elastomer tensile strength measurement, elastomer elongation measurement, etc.

Generally, the elastomer specimens are tested for tensile strength at break by moving the elastomer specimens to a tensile strength testing station wherein a tensile strength test is carried out, e.g., a test similar to ASTM D2671 or ASTM D412. For example, the specimen is held at each end by a grasping mechanism (as discussed above with respect to the robotic assembly) and stretched under a predetermined force until, for example, the specimen breaks, and the tensile strength measurement is determined. This measurement is compared against a predetermined tensile strength measurement (at break) of an elastomer sample of the same material under substantially similar tensile strength testing conditions (and this predetermined measurement is stored in the computer library to establish a reference point from which subsequent elastomer compatability data can be assessed for different lubricating oil compositions).

Additionally, elastomer specimens of the same material which have been immersed in the same lubricating composition under the same testing conditions discussed above are tested for elongation at break to provide further elastomer compatability data. Generally, the elastomer specimens will be moved to an elongation testing station wherein an elongation test is carried out, e.g., a test similar to ASTM D2671 or ASTM D412. For example, the specimen is held at each end by a grasping mechanism (as discussed above with respect to the robotic assembly) and stretched until, for example, the specimen breaks, and the elongation measurement is determined. This measurement is compared against a predetermined elongation measurement (at break) of an elastomer sample of the same material under substantially similar elongation testing conditions (and this predetermined measurement is stored in the computer library to establish a reference point from which subsequent elastomer compatability data can be assessed for different lubricating oil compositions).

If desired, an assigned value of elastomer compatibility is programmed into the computer controller for "pass/fail" determination. Assigned pass/fail values can be selected based upon performance requirements for specific lubricant applications and prospective operating environments. If the test sample fails by having an excessively poor elastomer compatibility value with a specific elastomer, the test sample can be electronically marked and future testing of lubricant oil formulations having the same composition as the sample can be eliminated from further testing for other performance characteristics. By not retesting failed samples the system can be made to operate more efficiently, energy and time being spent only on samples which prospectively meet the desired product specifications.

If desired, the results of the method of the present invention can be monitored from a remote location, i.e., a location which is not in direct or at least in visual contact with the system operating the method of the invention. A remote location can be, for example, a central process control system or room which, as part of the overall system for use herein, monitors and controls the system as well as records the outputs of each of the results of the tests being carried out. In this way, it becomes possible for less interaction with personnel being stationed at the location of the system. Suitable data lines, with which the results of the output, as well as control commands, may be transmitted, are known.

Elastomer compatibility data regarding each of the compositions described herein can be stored in a relational database to provide a combinatorial lubricating oil composition library. Alternatively, the system may be electrically connected to a signal data collector comprising a computer microprocessor for system operation and control to collect the data from the various tests over an extended period of time to compile the combinatorial lubricating oil composition library. The database can be used to find optimum combinations for a desired product stream, and can be particularly useful when the desired product stream varies depending on market factors. When the product requirements change, appropriate combinations can be selected to prepare the desired product.

Relational database software can be used to correlate the identity of the additive(s) and/or lubricating oil compositions to the analytical elastomer compatibility data obtained therefrom. Numerous commercially available relational database software programs are available, for example, from Oracle, Tripos, MDL, Oxford Molecular ("Chemical Design"), IDBS ("Activity Base"), and other software vendors.

Relational database software is a preferred type of software for managing the data obtained during the methods described herein. However, any software that is able to create a "memory map" of each of the additives and compositions described herein and correlate that information with the information obtained from the elastomer compatability measurements can be used. This type of software is well known to those of skill in the art.

While the above description contains many specifics, these specifics should not be construed as limitations of the invention, but merely as exemplifications of preferred embodiments thereof. For example, elastomer compatability tests other than those described herein can be used to provide elastomer compatability data for the plurality of different samples tested. Those skilled in the art will envision many other embodiments within the scope and spirit of the invention as defined by the claims appended hereto.

What is claimed is:

1. A high throughput method for screening lubricating oil composition samples for compatibility with elastomers, under program control, comprising the steps of:
   (a) conducting molecular modeling of at least one base oil of lubricating viscosity and at least one lubricating oil additive to provide leading candidates of the at least one base oil of lubricating viscosity and the at least one lubricating oil additive for combination to formulate a leading candidate lubricating oil composition sample for testing;
   (b) containing a plurality of the leading candidate lubricating oil composition samples comprising (i) a major amount of at least one base oil of lubricating viscosity and (ii) a minor amount of at least one lubricating oil additive in varying percentages in a plurality of test receptacles;
   (c) providing at least one elastomer;
   (d) measuring the elastomer compatibility of each sample to provide elastomer compatibility data results for each sample; and,
   (e) outputting the results of step (d).

2. The method of claim 1, wherein the at least one base oil of lubricating viscosity is a natural or synthetic oil.

3. The method of claim 1, wherein the at least one lubricating oil additive is selected from the group consisting of antioxidants, anti-wear agents, detergents, rust inhibitors, dehazing agents, demulsifying agents, metal deactivating agents, friction modifiers, pour point depressants, antifoaming agents, co-solvents, package compatibilisers, corrosion-inhibitors, ashless dispersants, dyes, extreme pressure agents and mixtures thereof.

4. The method of claim 1, wherein the at least one elastomer is selected from the group consisting of olefinic elastomers, styrenic elastomers, poly(ether/ester) elastomers, polyacrylate elastomers, natural rubbers, synthetic rubbers, elastomer seals and mixtures thereof.

5. The method of claim 1, wherein the at least one elastomer is an elastomer seal.

6. The method of claim 1, wherein the step of measuring the elastomer compatibility of each sample comprises immersing the at least one elastomer in the sample at a predetermined temperature for a predetermined period of time and measuring the tensile strength and/or elongation of the elastomer to determine the elastomer compatibility of the sample.

7. The method of claim 6, wherein the predetermined temperature is about 100° C. to about 400° C. and the predetermined time is about 100 hours to about 400 hours.

8. The method of claim 1, wherein the elastomer compatability measurement of step (c) comprises a tensile strength measurement or an elongation measurement.

9. The method of claim 8, wherein the tensile strength measurement is compared with a predetermined tensile strength measurement of the elastomer.

10. The method of claim 8, wherein the elongation measurement is compared with a predetermined elongation measurement of the elastomer.

11. The method of claim 1, wherein the lubricating oil composition test samples have a volume of no more than about 50 ml.

12. The method of claim 1, wherein the lubricating oil composition test samples have a volume of no more than about 20 ml.

13. The method of claim 1, wherein the lubricating oil composition test samples have a volume of no more than about 15 ml.

14. The method of claim 1, wherein the lubricating oil composition test samples have a volume of no more than about 10 ml.

15. The method of claim 6, further comprising thermally conditioning the elastomer prior to immersing the elastomer in the sample.

16. The method of claim 15, wherein the elastomer is thermally conditioned at a temperature of about 100° C. to about 200° C. for about 20 hours to about 60 hours.

17. The method of claim 1, wherein a robotic assembly selectively retrieves the individual test receptacles from an array of test receptacles and selectively retrieves the at least one elastomer and individually positions the test receptacles and the at least one elastomer in a testing station for determination of the elastomer compatibility.

18. The method of claim 17, wherein the robotic assembly is controlled by a computer.

19. The method of claim 1, wherein the step of outputting comprises storing the results of step (d) on a data carrier.

20. The method of claim 1, further comprising the step of using the result results of step (e) as a basis for obtaining a result of further calculations.

21. The method of claim 1, wherein the at least one lubricating oil additive of the lubricating oil composition further comprises a diluent oil to form an additive concentrate.

* * * * *